United States Patent
Park (10) Patent No.: US 12,151,122 B1
(45) Date of Patent: Nov. 26, 2024

(54) LASER NEEDLE TREATMENT SYSTEM

(71) Applicant: In Kyu Park, Busan (KR)

(72) Inventor: In Kyu Park, Busan (KR)

(*) Notice: Subject to any disclaimer, the term of this patent is extended or adjusted under 35 U.S.C. 154(b) by 0 days.

(21) Appl. No.: 18/018,726

(22) PCT Filed: Mar. 16, 2021

(86) PCT No.: PCT/KR2021/003266
§ 371 (c)(1),
(2) Date: Aug. 4, 2023

(87) PCT Pub. No.: WO2022/025383
PCT Pub. Date: Feb. 3, 2022

(30) Foreign Application Priority Data

Jul. 30, 2020 (KR) .................. 10-2020-0095563

(51) Int. Cl.
*A61N 5/06* (2006.01)
*A61N 5/067* (2006.01)

(52) U.S. Cl.
CPC .......... *A61N 5/0619* (2013.01); *A61N 5/067* (2021.08); *A61N 2005/066* (2013.01)

(58) Field of Classification Search
CPC . A61N 5/0619; A61N 5/067; A61N 2005/066
(Continued)

(56) References Cited

U.S. PATENT DOCUMENTS 6,355,054 B1 * 3/2002 Neuberger ........... A61B 18/203
604/20
2007/0005119 A1 1/2007 Crohn
(Continued)

FOREIGN PATENT DOCUMENTS

JP     S62139674 A    6/1987
JP     2016537133 A   12/2016
(Continued)

OTHER PUBLICATIONS

Moonseok Kim et al, Optical lens-microneedle array for percutaneous light delivery, Biomed Opt Express, 2016, vol. 7, Issue 10, pp. 4220-4227, Biomedical Optics Express, Washington, DC, USA.
(Continued)

*Primary Examiner* — Aaron F Roane
(74) *Attorney, Agent, or Firm* — STIP Law Group, LLC (57) ABSTRACT

A laser needle treatment system according to the present invention comprises: an optical cable connected to a laser generator and providing a laser generated by the laser generator; a hand piece in which a plurality of lenses for amplifying or extending the laser provided from the optical cable are installed; and a needle unit connected to the bottom of the hand piece to receive a laser through the hand piece and pass through the skin surface so as to directly emit the laser intradermally to an operation area, wherein the hand piece comprises: a focus lens to which the laser provided from the optical cable is incident; a convex lens for extending or amplifying a laser emitted from the focus lens; a collimator lens for emitting the laser emitted from the convex lens to be parallel to a proceeding direction; and an optical lens part connected to the needle unit and including a plurality of optical lenses Installed therein to extend or amplify a laser emitted from the collimator lens and transmit the same to the needle unit.

4 Claims, 6 Drawing Sheets

(58) Field of Classification Search
USPC .......................................................... 607/89
See application file for complete search history.

(56) References Cited

U.S. PATENT DOCUMENTS

| | | | |
|---|---|---|---|
| 2012/0022367 A1 | 1/2012 | Wong | |
| 2013/0066300 A1 | 3/2013 | Rhee | |
| 2016/0199132 A1* | 7/2016 | Anderson | ............ A61B 18/203 |
| | | | 606/9 |

FOREIGN PATENT DOCUMENTS

| | | |
|---|---|---|
| KR | 100914142 B1 | 8/2009 |
| KR | 20100009154 A | 1/2010 |
| KR | 20100101420 A | 9/2010 |
| KR | 101088490 B1 | 11/2011 |
| KR | 20150025543 A | 3/2015 |
| KR | 20170087490 A | 7/2017 |
| KR | 101924492 B1 | 12/2018 |
| KR | 102151923 B1 | 9/2020 |

OTHER PUBLICATIONS

International search report of PCT/KR2021/003266, Jul. 5, 2021, English translation.

\* cited by examiner

LASER NEEDLE TREATMENT SYSTEM

CROSS-REFERENCE TO RELATED APPLICATIONS

This application is the U.S. National Phase under 35 U.S.C. § 371 of International Application No. PCT/KR2021/003266, filed on Mar. 16, 2021, which in turn claims the benefit of Korean Application No. 10-2020-0095563, filed on Jul. 30, 2020, the disclosures of which are incorporated by reference into the present application.

TECHNICAL FIELD

The present invention relates to a needle laser treatment system.

BACKGROUND ART

Generally, treatment methods using electric acupuncture, magnetic field (or magnet) acupuncture, infrared acupuncture, ultrasonic acupuncture, or the like by means of electricity, magnetic fields, infrared rays, laser beams, ultrasounds, or the like as a treatment means are used.

These treatment methods are non-invasive methods that can obtain stimulating effects by applying electric current, magnetic fields, infrared rays, ultrasonic waves, or the like to a lesion.

However, the treatment methods using the conventional electric acupuncture, magnetic acupuncture, infrared acupuncture, ultrasonic acupuncture, or the like described above are medical procedures for non-invasively stimulating a lesion, and a higher treatment effect could not be expected compared to an invasive medical procedure.

In addition, in order to overcome the disadvantages in the effect of the non-invasive medical procedures described above, invasive medical procedures of inserting a needle of a very small diameter into the skin of a lesion and directly applying current, magnetic fields, infrared rays, ultrasounds, or the like to the lesion are performed.

However, the demand and necessity for laser needles that can minimize the pain of a patient caused by direct invasion, vary the treatment effects according to the depth of insertion of the needles, and enhance the treatment effects are increasing recently in the invasive medical procedures.

In relation to this, a prior art is disclosed in Korean Patent Registration No. 10-1088490 (published on Nov. 30, 2011).

The prior art relates to an invasive needle manufactured by electroplating a metal on an optical fiber and a method of manufacturing the same, which is a technique of providing an invasive needle electroplated with a metal on an optical fiber to replace metal needles and improve low treatment effects of non-invasive laser needles.

However, since the conventional technique uses a single laser needle, there is a problem of lowering the effect of acupuncture treatment, extending the time of medical procedures, or the like, and as it is difficult to directly transfer high-frequency laser beams to a target layer, which is an area of a medical procedure, there is a problem of lowering the effect of the medical procedure.

DISCLOSURE OF INVENTION

Technical Problem

Therefore, the present invention has been made in view of the above problems, and it is an object of the present invention to provide a needle laser treatment system capable of greatly improving the effect of medical procedure and treatment as a high-frequency laser beam can be efficiently transferred to an area of medical procedure while the medical procedure can be performed easily by using a plurality of needles.

Technical Solution

To accomplish the above object, according to one aspect of the present invention, there is provided a needle laser treatment system comprising: an optical cable connected to a laser beam generator to provide a laser beam generated by the laser beam generator; a hand piece having a plurality of lenses installed therein to amplify or extend the laser beam received from the optical cable; and a needle unit connected to the bottom of the hand piece to receive the laser beam through the hand piece, pass the laser beam through the skin surface, and directly irradiate the laser bear to an area of medical procedure in the skin, wherein the hand piece comprises: a focus lens through which the laser beam received from the optical cable enters; a convex lens for extending or amplifying the laser beam emitted from the focus lens; a collimate lens for emitting the laser beam emitted from the convex lens to be parallel to the traveling direction; and an optical lens unit connected to the needle unit and having a plurality of optical lenses installed therein to extend or amplify the laser beam emitted from the collimate lens and transfer the laser beam to the needle unit.

In the needle laser treatment system according to an embodiment of the present system, the needle unit may comprise: a frame formed hollow and made of a transparent material to be detachably installed on the bottom of the handpiece; a plurality of needle elements arranged inside the frame to emit the laser beam transferred through the plurality of optical lenses so that the laser beam may pass through the skin surface and be directly irradiated on an area of medical procedure in the skin; a circuit board unit arranged on an inner upper side of the frame, electrically connected to the needle elements, and having the plurality of needle elements installed therein; a control unit electrically connected to the circuit board unit to control the operation of the needle elements and the circuit board unit; and a guide unit installed to be spaced apart from the circuit board by a predetermined distance in the downward direction of the frame, and having a plurality of holes, through which the plurality of needle elements may pass, formed to guide the vertical operation path of the needle elements and the circuit board unit.

In the needle laser treatment system according to an embodiment of the present system, the needle unit may further comprise a guide bar installed between the circuit board unit and the guide unit and having a spring installed therein to support the needle elements to smoothly move up and down.

In the needle laser treatment system according to an embodiment of the present system, the needle element may be provided to have a diameter of 0.4 mm, and have a needle hole formed therein to have a diameter of 0.27 mm, and the needle element may be configured to pass through the skin surface and directly irradiate the laser beam to the area of medical procedure in the skin as a fiber optic bar having a diameter of 0.25 mm is inserted into the needle hole.

In the needle laser treatment system according to an embodiment of the present system, as many needle elements as the number of the optical lenses of the optical lens unit may be configured.

Advantageous Effects

As the needle element passes through the skin surface and is deeply inserted into the skin to efficiently transfer a high-frequency laser beam to an area of medical procedure, the present invention may greatly improve the effect of medical procedure and treatment.

As the needle element may pass through the skin surface and directly penetrate into an area of medical procedure (dermis layer) in the skin to emit RF energy and laser energy in the skin, the present invention may provide various effects of medical procedure.

As a plurality of lenses is installed in a handpiece to efficiently transfer a laser beam received from an optical cable to a plurality of needle elements while extending or amplifying the laser beam, the present invention may improve the effect of laser treatment.

BEST MODE FOR CARRYING OUT THE INVENTION

Hereinafter, when it is determined that a detailed description of a related known technique may unnecessarily obscure the gist of the present invention, the detailed description will be omitted. In addition, the numbers used in describing this specification are only reference symbols for distinguishing one component from another component.

In addition, the terms used in this specification and claims should not be construed as being limited to dictionary meanings, and based on the principle that the inventor may properly define the concept of terms in order to explain his/her invention in the best way, the terms should be interpreted as a meaning or a concept that meets the technical spirit of the present invention.

Accordingly, as the embodiments described in this specification and the configurations shown in the drawings are only preferred embodiments of the present invention, and do not express all the technical spirits of the present invention, it should be understood that there may be various equivalents and modifications that can replace those at the time of this application.

A preferred embodiment of the present invention will be described in more detail, and already known technical parts will be omitted or compressed for brevity of description.

Figure 1:
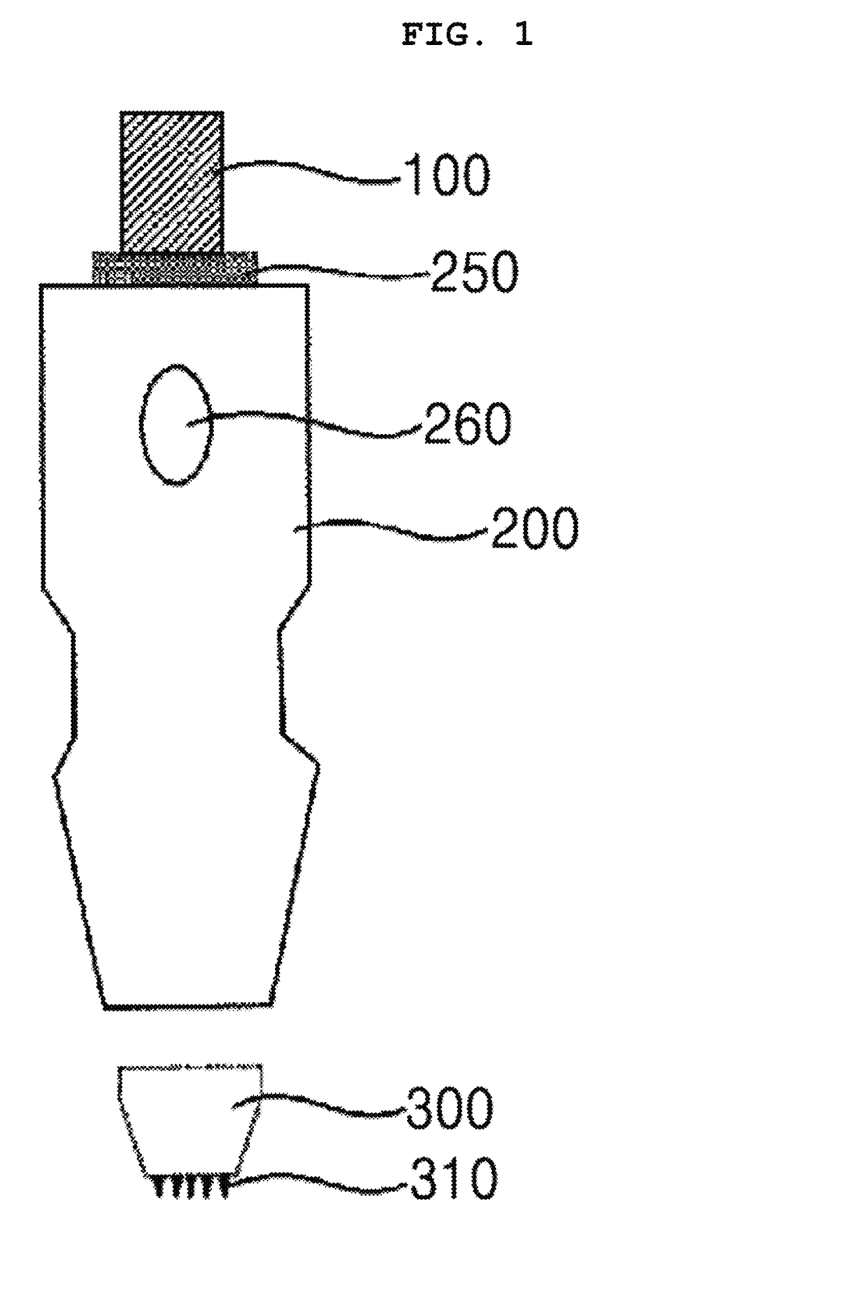
FIG. 1 is a view showing a schematic configuration of a needle laser treatment system according to an embodiment of the present invention.
Figure 2:
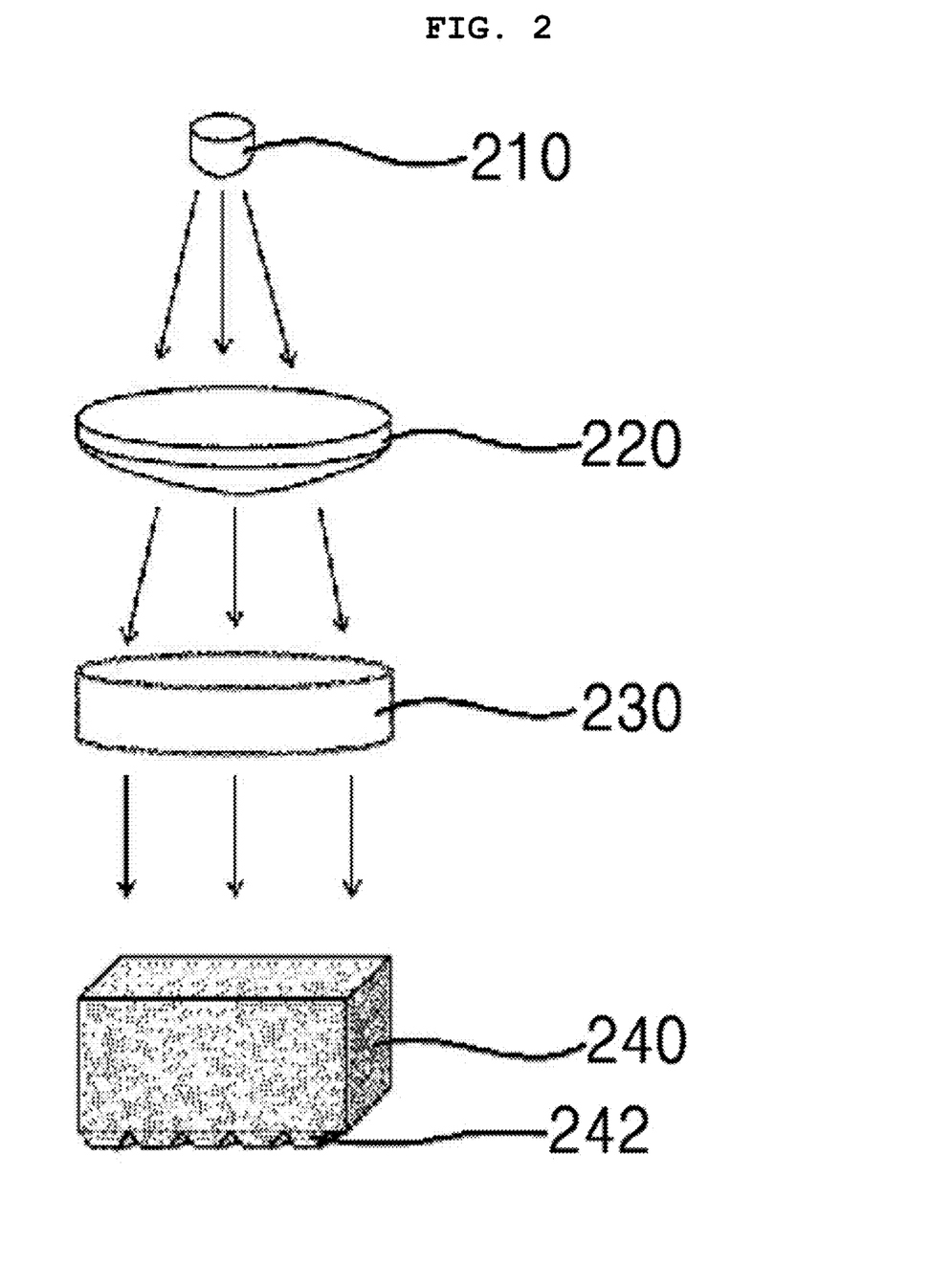
FIG. 2 is a view showing a plurality of lenses in a handpiece of a needle laser treatment system according to an embodiment of the present invention.
Figure 3:
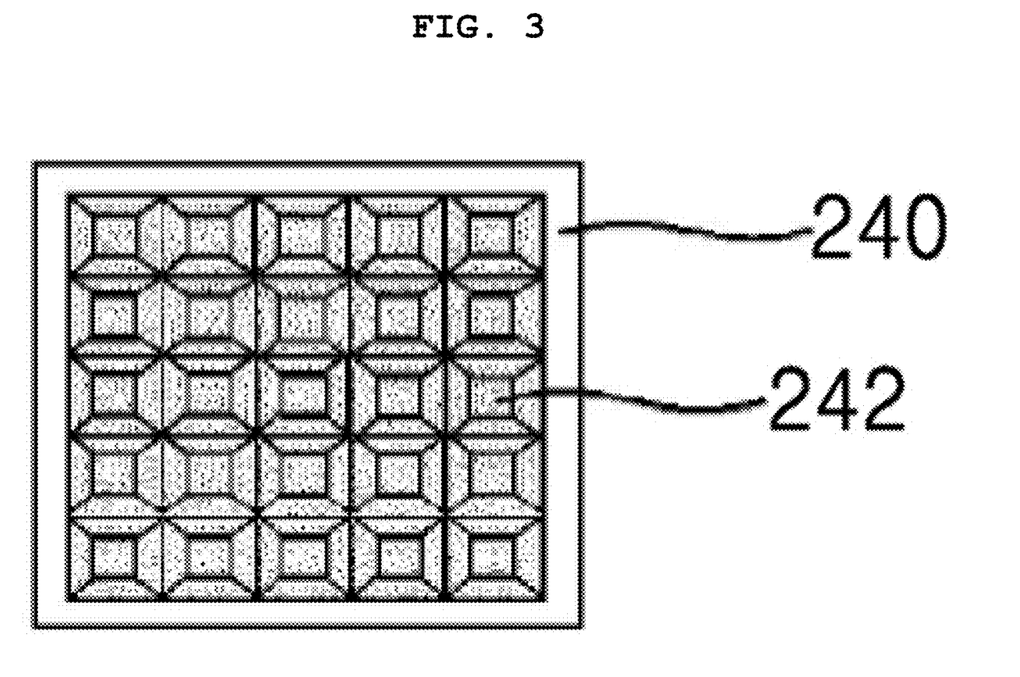
FIG. 3 is a view showing an optical lens unit of a needle laser treatment system according to an embodiment of the present invention.
Figure 4:
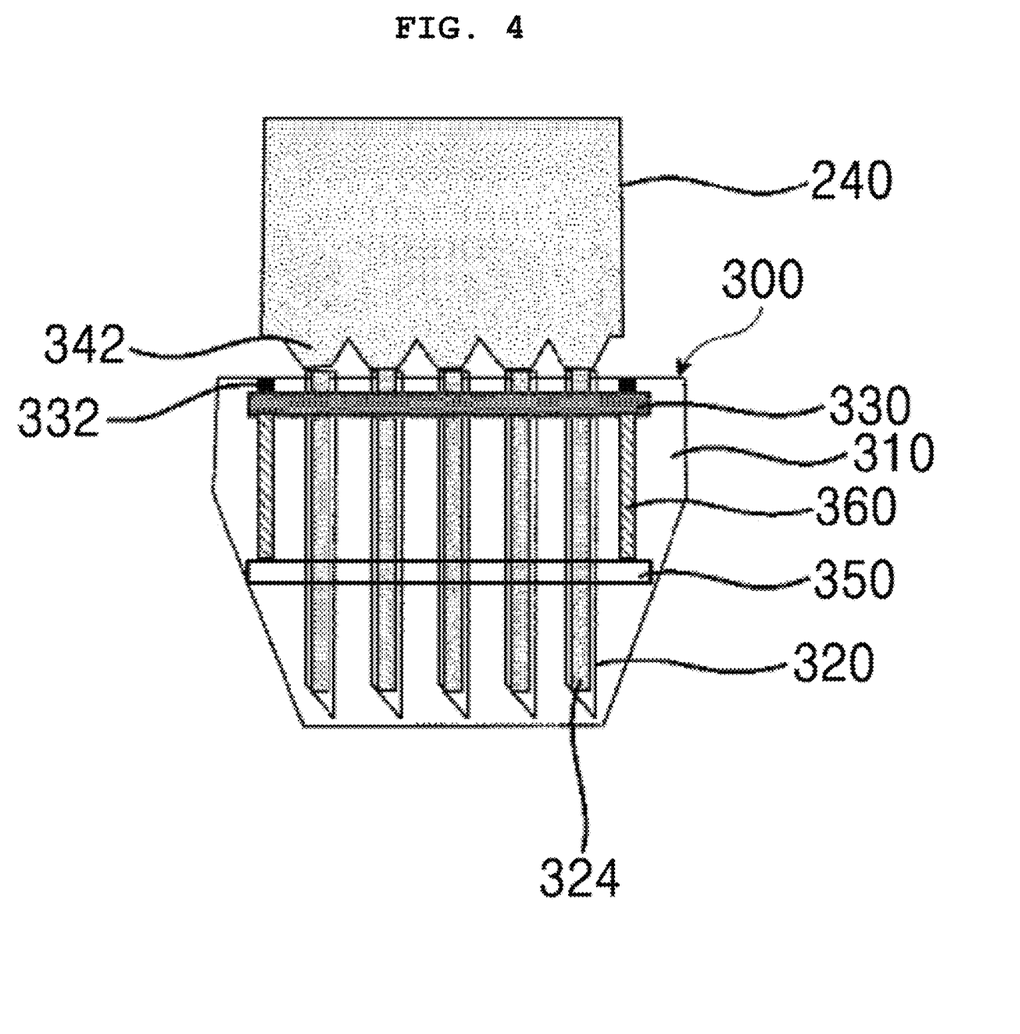
FIG. 4 is a view showing an optical lens unit and a needle unit of a needle laser treatment system according to an embodiment of the present invention.
Figure 5:
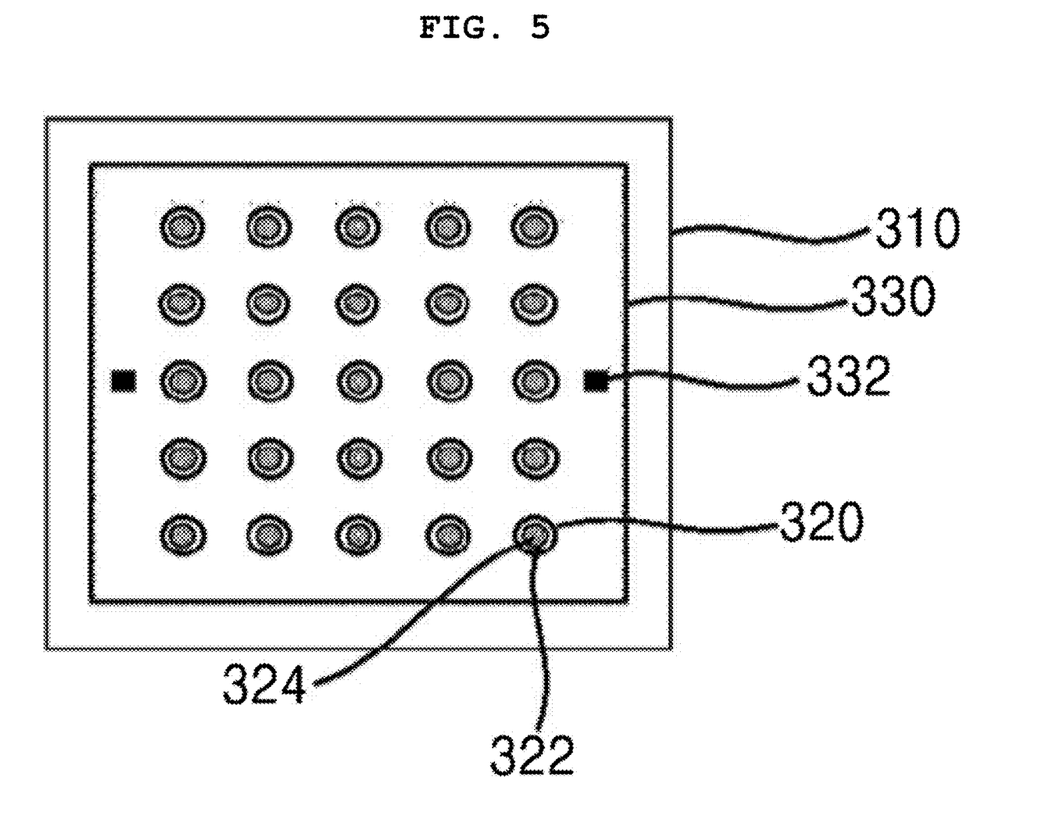
FIG. 5 a view showing a needle unit of a needle laser treatment system according to an embodiment of the present invention.
Figure 6:
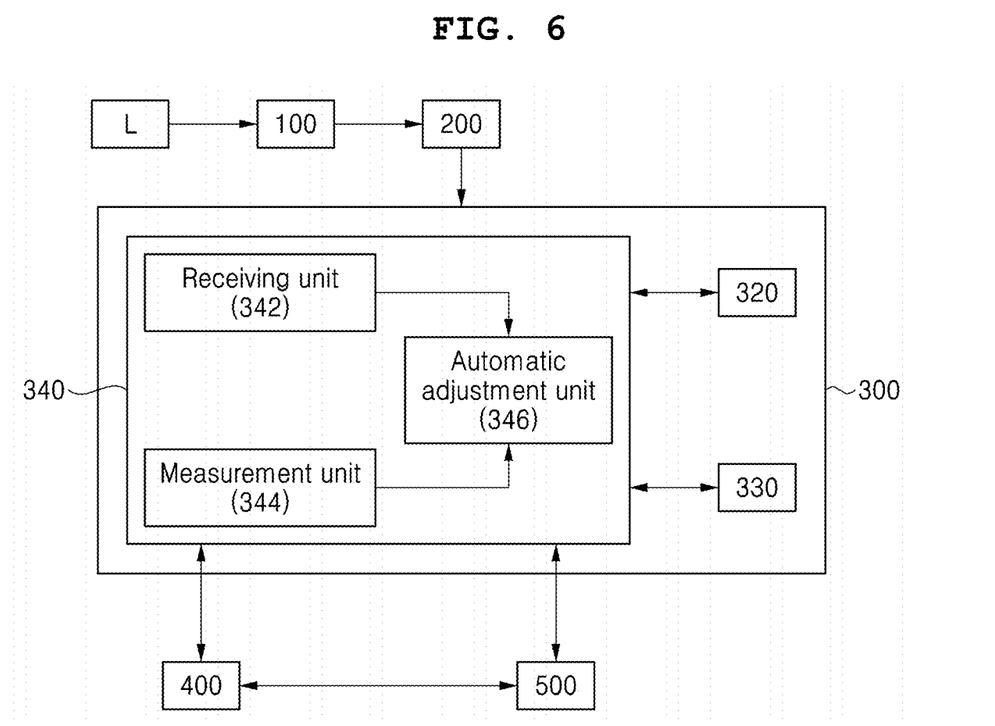
FIG. 6 is a block diagram showing a schematic configuration of a needle laser treatment system according to an embodiment of the present invention.

FIG. 1 is a view showing a schematic configuration of a needle laser treatment system according to an embodiment of the present invention, FIG. 2 is a view showing a plurality of lenses in a handpiece 200 of a needle laser treatment system according to an embodiment of the present invention, FIG. 3 is a view showing an optical lens unit 240 of a needle laser treatment system according to an embodiment of the present invention, FIG. 4 is a view showing an optical lens unit 240 and a needle unit 300 of a needle laser treatment system according to an embodiment of the present invention, FIG. 5 a view showing a needle unit 300 of a needle laser treatment system according to an embodiment of the present invention, and FIG. 6 is a block diagram showing a schematic configuration of a needle laser treatment system according to an embodiment of the present invention.

A needle laser treatment system according to an embodiment of the present invention comprises: an optical cable 100 connected to a laser beam generator L to provide a laser beam generated by the laser beam generator L; a hand piece 200 having a plurality of lenses installed therein to amplify or extend the laser beam received from the optical cable 100; and a needle unit 300 connected to the bottom of the hand piece 200 to receive the laser beam through the hand piece 200, pass the laser beam through the skin surface, and directly irradiate the laser beam to an area of medical procedure in the skin, and the hand piece 200 comprises: a focus lens 210 through which the laser beam received from the optical cable 100 enters; a convex lens 220 for extending or amplifying the laser beam emitted from the focus lens 210; a collimate lens 230 for emitting the laser beam emitted from the convex lens 220 to be parallel to the traveling direction; and an optical lens unit 240 connected to the needle unit 300 and having a plurality of optical lenses installed therein to extend or amplify the laser beam emitted from the collimate lens 230 and transfer the laser beam to the needle unit 300.

The optical cable 100 is a component connected to the laser beam generator L to provide the laser beam generated by the laser beam generator L to the hand piece 200 and the needle unit 300, and may be configured to comprise an optical fiber therein. In addition, the optical cable 100 may comprise a cable electromotive force (EMF) to transfer high-frequency energy to the hand piece 200 and the needle unit 300.

The handpiece 200 is a component having a plurality of lenses installed therein to amplify or extend the laser beam received from the optical cable 100, and may be made of a plastic material. In addition, glossy coating may be performed on the outer surface of the handpiece 200.

The plurality of lenses installed inside the handpiece 200 comprises a focus lens 210, a convex lens 220, a collimate lens 230, and an optical lens unit 240, and the laser beam received from the optical cable 100 may passes through the lenses in order.

The focus lens 210 is a component through which the laser beam received from the optical cable 100 enters, and is a component for diffusing and emitting the incident laser beam.

The convex lens 220 is a component for extending or amplifying the laser beam emitted from the focus lens 210.

The collimate lens 230 is a component for emitting the laser beam emitted from the convex lens 220 to be parallel to the traveling direction, and emitting the laser beam emitted to be parallel to the optical lens unit 240.

The optical lens unit 240 is a component connected to the needle unit 300, and having a plurality of optical lenses installed therein to extend or amplify the laser beam emitted from the collimate lens 230 and transfer the laser beam to the needle unit 300.

Specifically, the optical lens unit 240 has a plurality of optical lenses inserted therein, and may be configured to comprise a convex portion 242 directly connected to the needle unit 300.

Here, the convex portion 242 may be provided in the form of crystal and configured to transfer the laser beam entered in a wide range through the collimate lens 230 to the plurality of needle elements 320. That is, as the optical lens unit 240 is configured to contact one needle element 320 to one convex portion 242 configured at the rear end while passing most of the laser beam emitted from the collimating lens 230, it may directly transfer the laser beam emitted through the optical lens arranged inside the convex portion 242 to the needle elements 320.

Accordingly, it is preferable that the number of the convex portions 242 is the same as the number of the needle elements 320, and in an embodiment of the present invention, the number of the convex portions 242 and the needle elements 320 may be twenty-five.

As described above, as a plurality of lenses is installed in the handpiece 200 to efficiently transfer the laser beam received from the optical cable 100 to a plurality of needle elements 320 while extending or amplifying the laser beam, the present invention may improve the effect of laser treatment.

Meanwhile, a connection unit 250 of a synthetic resin material for connecting the optical cable 100 may be configured on the top of the handpiece 200.

In addition, a button unit 260 for controlling on/off of the hand piece 200 and the needle element 320 may be installed on one side of the outer surface of the hand piece 200 to start or stop the procedure of needle treatment.

In the needle laser treatment system according to an embodiment of the present system, the needle unit 300 may comprise: a frame 310 formed hollow and made of a transparent material to be detachably installed on the bottom of the handpiece 200; a plurality of needle elements 320 arranged inside the frame 310 to emit the laser beam transferred through the plurality of optical lenses so that the laser beam may pass through the skin surface and be directly irradiated on an area of medical procedure in the skin; a circuit board unit 330 arranged on the inner upper side of the frame 310, electrically connected to the needle elements 320, and having the plurality of needle elements 320 installed therein; a control unit 340 electrically connected to the circuit board unit 330 to control the operation of the needle elements 320 and the circuit board unit 330; and a guide unit 350 installed to be spaced apart from the circuit board by a predetermined distance in the downward direction of the frame 310, and having a plurality of holes, through which the plurality of needle elements 320 may pass, formed to guide the vertical operation path of the needle elements 320 and the circuit board unit 330.

In the needle laser treatment system according to an embodiment of the present system, the needle unit 300 may further comprise a guide bar 360 installed between the circuit board unit 330 and the guide unit 350 and having a spring installed therein to support the needle elements 320 to smoothly move up and down.

In the needle unit 300, the frame 310 is a component formed hollow, made of a transparent material, and detachably installed on the bottom of the handpiece 200, and may be made of a non-conductive synthetic resin material.

The needle element 320 is a component arranged inside the frame 310 to emit the laser beam transferred through the plurality of optical lenses so that the laser beam may pass through the skin surface and be directly irradiated on an area of medical procedure in the skin, and may be provided in plurality.

Here, the needle element 320 may be configured to pass through the skin surface and directly penetrate into an area of medical procedure (dermis layer) in the skin to emit RF energy and laser energy in the skin. The depth of the needle element 320 inserted into the skin may be up to 3.5 mm.

In addition, it may be configured to emit the laser beam emitted through the needle element 320 at various wavelengths.

That is, the wavelength of the laser beam emitted through the needle element 320 may be 1450 to 1550 nm for lifting improvement, acne treatment, scar treatment, or the like, and may be 530 to 590 nm for treatment of pigmentation and redness of the skin and improvement of the functions of blood vessels.

Meanwhile, in the needle laser treatment system according to an embodiment of the present system, the needle element 320 is provided to have a diameter of 0.4 mm, and has a needle hole 322 formed therein to have a diameter of 0.27 mm, and the needle element 320 may be configured to pass through the skin surface and directly irradiate the laser beam to an area of medical procedure in the skin as a fiber optic bar 324 having a diameter of 0.25 mm is inserted into the needle hole 322.

That is, as the needle element 320 passes through the skin surface and is deeply inserted into the skin to efficiently transfer a high-frequency laser beam to an area of medical procedure, the present invention may greatly improve the effect of medical procedure and treatment.

In addition, since the laser beam enters from the optical lenses, it is preferable to provide as many needle elements 320 as the number of the optical lenses and convex portions 242. In other words, it is preferable that as many needle elements 320 as the number of the optical lenses and convex portions 242 are provided.

The circuit board unit 330 is a component arranged on the inner upper side of the frame 310, electrically connected to the needle elements 320, and having the plurality of needle elements 320 installed therein. The plurality of needle elements 320 may be installed in the circuit board unit 330 by soldering, and may be configured as a PCB substrate.

The guide unit 350 is a component installed to be spaced apart from the circuit board by a predetermined distance in the downward direction of the frame 310, and having a plurality of holes, through which the plurality of needle elements 320 may pass, formed to guide the vertical operation path of the needle elements 320 and the circuit board unit 330. That is, in the present invention, the needle element 320 may smoothly move up and down along the hole formed in the guide unit 350. Accordingly, in the present invention, since the needle element 320 may move up and down along the guide of the guide unit 350 without being shaken left and right, the needle element 320 may be inserted into an accurate area of medical procedure, and thus enhance the effect of medical procedure.

In the needle unit 300, the guide bar 360 is a component installed between the circuit board unit 330 and the guide unit 350 and having a spring installed therein to support the needle elements 320 to smoothly move up and down. Accordingly, in the present invention, as the needle elements 320 may smoothly move up and down, the time of medical procedure can be reduced, and thus the medical procedure may be performed easily.

Meanwhile, substrate blocks 332 may be installed on both sides of the circuit board unit 330. It may be configured to couple one end of the substrate block 332 to the inner top of the frame 310 and connect the other end to the guide bar 360. Accordingly, in the present invention, the circuit board unit 330 may smoothly move up and down, together with the needle elements 320, by the guide bar 360.

The control unit 340 a component electrically connected to the circuit board unit 330 to control the operation of the needle elements 320 and the circuit board unit 330. That is, the control unit 340 is configured to control the up and down operation state of the needle elements 320 so that the needle elements 320 may be inserted into the skin.

In the present invention, the needle laser treatment system may further comprise an input device 400 configured to input the depth of the needle element 320 inserted into the skin as a numerical value according to implementation.

Accordingly, the control unit 340 may be configured to comprise: a receiving unit 342 for receiving the numerical value input into the input device 400; a measurement unit 344 for measuring the depth of the needle element 320 actually inserted into the skin; and an automatic adjustment unit 346 for controlling the operation of the needle element 320 to automatically adjust the degree of the needle element 320 inserted into the skin by comparing the numerical value received through the receiving unit 342 and the measurement value measured through the measurement unit 344.

That is, as the depth of the needle element 320 inserted into the skin can be accurately and automatically adjusted through the control unit 340, the present invention may further enhance the accuracy and effect of the medical procedure.

In addition, the present invention may further comprise a display device 500 for displaying the depth of the needle element 320 inserted into the skin in order to adjust the depth inserted into the skin when the needle element 320 is inserted into the skin under the control of the controller 340.

The display device 500 may be configured to display the numerical value input through the input device 400, the measurement value measured through the measurement unit 344, and the value of the length of the inserted needle element 320 adjusted through the automatic adjustment unit 346. Therefore, an operator may easily know various values through the display device 500, and perform medical procedures more efficiently.

INDUSTRIAL APPLICABILITY

Although the detailed description of the present invention has been accomplished as an embodiment as described above, as the embodiment described above have only been described with preferred examples of the present invention, it should not be understood that the present invention is limited only to the embodiment described above, and the scope of the present invention should be understood as the claims described below and equivalent concepts thereof.

DESCRIPTION OF SYMBOLS

| L: Laser beam generator | 100: Optical cable |
| 200: Hand piece | 210: Focus lens |
| 220: Convex lens | 230: Collimate lens |
| 240: Optical lens unit | 242: Convex portion |
| 250: Connection unit | 260: Button unit |
| 300: Needle unit | 310: Frame |
| 320: Needle element | 322: Needle hole |
| 324: Fiber optic bar | 330: Circuit board unit |
| 332: Substrate block | 340: Control unit |
| 342: Receiving unit | 344: Measurement unit |
| 346: Automatic adjustment unit | 350: Guide unit |
| 360: Guide bar | 400: Input device |
| 500: Display device | |

The invention claimed is:

1. A needle laser treatment system comprising:
an optical cable connected to a laser beam generator to provide a laser beam generated by the laser beam generator;
a hand piece having a plurality of lenses installed therein to extend the laser beam received from the optical cable; and
a needle unit connected to a bottom of the hand piece to receive the laser beam through the hand piece, pass the laser beam through the skin surface, and directly irradiate the laser beam to an area of medical procedure in the skin, wherein
the hand piece comprises:
a focus lens through which the laser beam received from the optical cable is entered and directed in the opposite direction;
a convex lens for extending the laser beam emitted from the focus lens;
a collimate lens for emitting the laser beam emitted from the convex lens to be parallel to a traveling direction; and
an optical lens unit connected to the needle unit and having a plurality of optical lenses installed therein to transfer the laser beam emitted from the collimate lens to the needle unit and the plurality of optical lenses comprises a convex portion directly connected to the needle unit, wherein
the needle unit comprises:
a frame formed hollow and made of a transparent material to be detachably installed on a bottom of the handpiece;
a plurality of needle elements arranged inside the frame to emit the laser beam transferred through the plurality of optical lenses so that the laser beam may pass through the skin surface and be directly irradiated on an area of medical procedure in the skin;
a circuit board unit arranged on an inner upper side of the frame, electrically connected to the needle elements, and having the plurality of needle elements installed therein;
a control unit electrically connected to the circuit board unit to control operation of the needle elements and the circuit board unit; and
a guide unit installed to be spaced apart from the circuit board by a predetermined distance in a downward direction of the frame, and having a plurality of holes, through which the plurality of needle elements may pass, formed to guide a vertical operation path of the needle elements and the circuit board unit.

2. The system according to claim 1, wherein the needle unit further comprises a guide bar installed between the circuit board unit and the guide unit and having a spring installed therein to support the needle elements to smoothly move up and down.

3. The system according to claim 2, wherein the needle element is provided to have a diameter of 0.4 mm, and has a needle hole formed therein to have a diameter of 0.27 mm, and the needle element is configured to pass through the skin surface and directly irradiate the laser beam to the area of medical procedure in the skin as a fiber optic bar having a diameter of 0.25 mm is inserted into the needle hole.

4. The system according to claim 1, wherein as many needle elements as the number of the optical lenses of the optical lens unit are configured.

\* \* \* \* \*